US008888822B2

(12) United States Patent
Loftus et al.

(10) Patent No.: US 8,888,822 B2
(45) Date of Patent: Nov. 18, 2014

(54) METHOD FOR PERFORMING MINIMALLY INVASIVE SURGERY

(76) Inventors: Thomas Stuart Loftus, Austin, TX (US); James Scott Hay, Parkland, FL (US); Ryan Singh, Loxahatchee, FL (US)

(*) Notice: Subject to any disclaimer, the term of this patent is extended or adjusted under 35 U.S.C. 154(b) by 352 days.

(21) Appl. No.: 13/440,908

(22) Filed: Apr. 5, 2012

(65) Prior Publication Data
US 2012/0197300 A1     Aug. 2, 2012

Related U.S. Application Data

(63) Continuation of application No. 12/584,248, filed on Sep. 2, 2009, now Pat. No. 8,182,519.

(51) Int. Cl.
| | | |
|---|---|---|
| A61B 17/88 | (2006.01) | |
| A61B 17/02 | (2006.01) | |
| A61B 17/70 | (2006.01) | |
| A61B 1/32  | (2006.01) | |

(52) U.S. Cl.
CPC ......... *A61B 17/7076* (2013.01); *A61B 17/0206* (2013.01); *A61B 17/0293* (2013.01); *A61B 1/32* (2013.01)

USPC .......................................................... 606/279

(58) Field of Classification Search
USPC ........ 600/184–246; 606/60, 70, 71, 246–279, 606/300–331; 623/17.11–17.16
See application file for complete search history.

(56) References Cited

U.S. PATENT DOCUMENTS

| | | | | |
|---|---|---|---|---|
| 5,928,139 A * | 7/1999 | Koros et al. | ................... | 600/205 |
| 2008/0114403 A1 * | 5/2008 | Kuester et al. | ................ | 606/308 |

* cited by examiner

*Primary Examiner* — Christopher Beccia
(74) *Attorney, Agent, or Firm* — David O. Simmons

(57) ABSTRACT

Pedicle screw apparatuses each including a pedicle screw assembly and an attached pedicle screw extender are placed in a true percutaneous manner, thereby overcoming issues resulting from placing pedicle screw assemblies through a retractor. Thus, a retractor can advantageously be built off of the pedicle screw apparatuses, thereby allowing visualization of the spine anatomy directly. Furthermore, such a method for performing surgery ensures ideal placement of the retractor for additional procedures that are often required such as, for example, decompression, interbody device placement, etc.

16 Claims, 13 Drawing Sheets

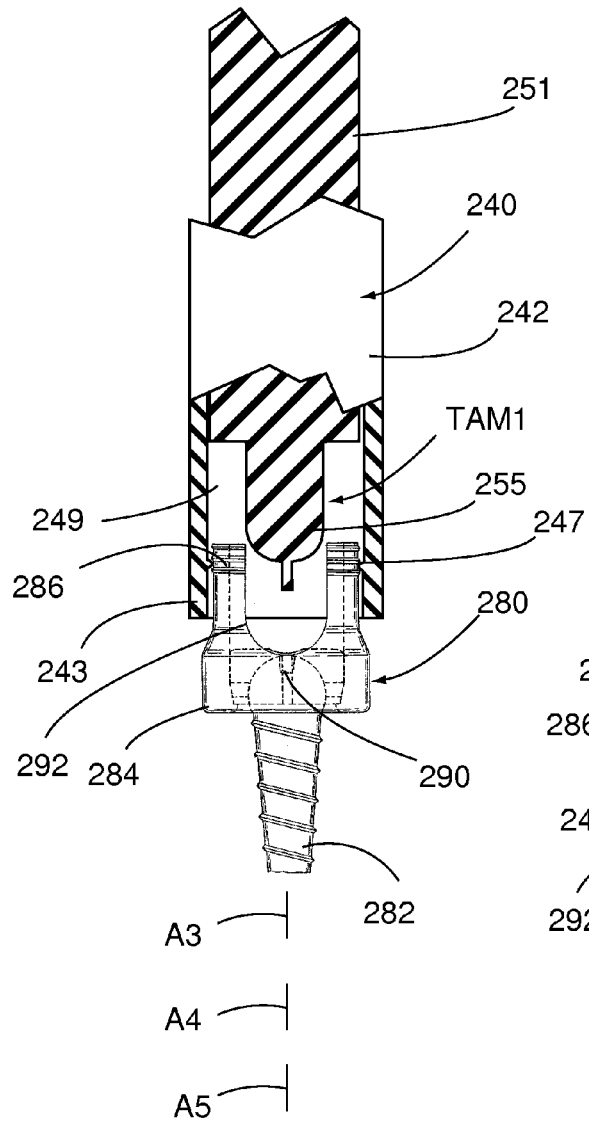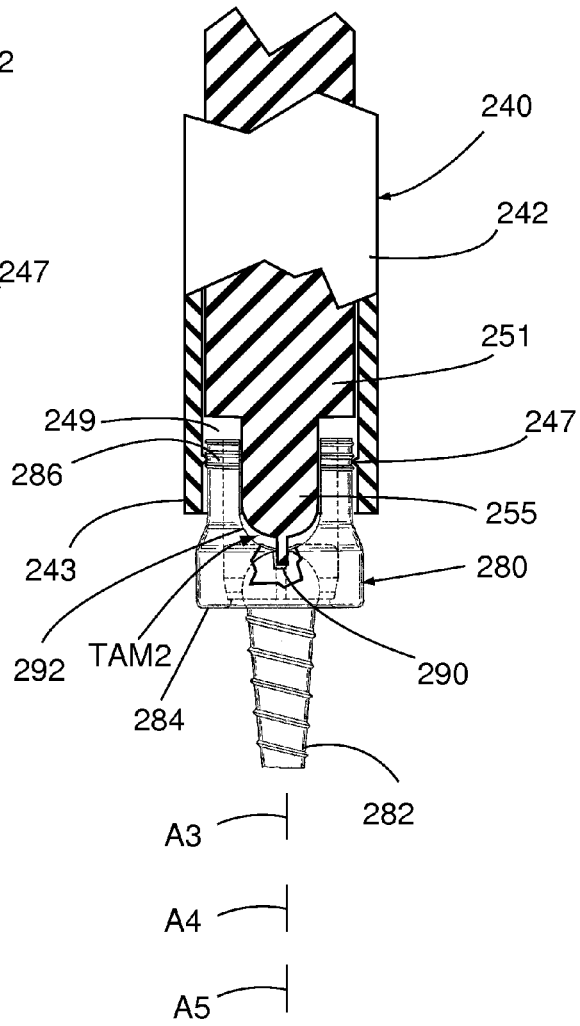

METHOD FOR PERFORMING MINIMALLY INVASIVE SURGERY

CROSS REFERENCE TO RELATED APPLICATIONS

This continuation patent application claims priority from co-pending United States Non-Provisional Patent Application having Ser. No. 12/584,248 filed Aug. 2, 2009 entitled "Method For Performing Minimally Invasive Surgery", which has a common applicant herewith and is being incorporated herein in its entirety by reference.

FIELD OF THE DISCLOSURE

The disclosures made herein relate generally to components, systems and apparatuses used for orthopedic and other types of invasive surgery and, more particularly, to components, systems and apparatuses used in performing minimally invasive spinal surgery.

BACKGROUND

A minimally invasive surgical procedure is a surgical procedure that is less invasive than open surgery used for the same type of procedure. Minimally invasive surgery is typically performed through several small incisions (e.g., slits, punctures or the like) as opposed to one or more large incisions as is used in open surgery. In a typical minimally invasive spinal surgery, an endoscope and/or surgical instruments are passed through these incisions. The endoscope, which includes a thin, lighted tube with an attached camera, enables a surgeon to view an area being operated on using a monitor. Alternatively to using an endoscope or in conjunction with use of an endoscope, an operating microscope can be used. By performing the surgical procedure through small incisions, the surgeon can safely work on the site being operated on while disturbing only a minimal portion of surrounding tissue, organs, etc. As a result, patients are less likely to develop complications, they are more likely to recover more quickly, and can typically return to normal activities sooner in comparison to open surgery.

In performing minimally invasive surgical procedures of the spine (i.e., minimally invasive spine surgery), use of a refractor is often desirable or necessary. One current approach for minimally invasive spine surgery is to first install a refractor and then, through use of sequentially dilating tubes or other means, installing pedicle screws, fixation rods and/or the like through a passage defined by tissue retracted by the retractor. This approach has the drawback of less than accurate placement of the pedicle screw due to the distal end of the tubes not being precisely placable and/or the retractor causing inadequate visualization of the pedicle screws when using fluoroscopy.

Therefore, an approach configured for first percutaneously placing the pedicle screws and then building a retractor off of the pedicle screws would overcome drawbacks associated with prior art approaches for placing pedicle screws in minimally invasive spine surgery, thus making such approach advantageous, desirable and useful.

SUMMARY OF THE DISCLOSURE

Embodiments of the present invention include pedicle screw systems and method of use configured for being used in surgical procedures such as, for example, minimally invasive retractor system designed for lumbar spine fusion surgery, lumbar diskectomy surgery and the like. Such embodiments overcome adverse issues associated with prior art approaches of placing pedicle screw assemblies through a retractor. Such prior art approaches result in inadequate visualization of the pedicle using fluoroscopy through the retractor. It is disclosed herein that embodiments of the present invention are well suited for various types of spine-related surgical procedures and applications, but can also be used in other types of surgical procedures and applications. Accordingly, embodiments of the present invention are not unnecessarily limited to use in any particular type of surgical procedure or application.

In accordance with embodiments of the present invention, pedicle screw assemblies and pedicle screw extenders detachably attached to the pedicle screw assemblies are placed in a true percutaneous manner, thereby overcoming issues resulting from placing pedicle screw assemblies through a retractor. Accordingly, embodiments of the present invention advantageously allow retractor placement over a pedicle screw assembly/pedicle screw extender construct allows visualization of the spine anatomy directly. Furthermore, in accordance with embodiments of the present invention, building the retractor off the pedicle screw assemblies and attached pedicle screw extenders ensures ideal placement of the retractor for additional procedures that are often required (e.g., decompression, interbody device placement, etc).

In one embodiment of the present invention, a method for performing surgery can comprise a plurality of the following operations. An operation can be performed for providing a pedicle screw apparatus including a pedicle screw assembly having a first end portion of a pedicle screw extender attached thereto in a manner providing for simultaneous transfer of rotational torque applied thereto to a screw portion of the pedicle screw assembly and for maintaining a longitudinal axis of a fixation rod receiving body of the pedicle screw assembly in substantially coincidental alignment with a longitudinal axis of the screw portion. An operation can be performed for anchoring the pedicle screw assembly to a bony structure of a patient. Such anchoring includes using the pedicle screw extender to apply rotational torque to the screw portion of the pedicle screw assembly. An operation can be performed for engaging a blade body with the pedicle screw extender in a manner allowing the blade body to be moved along the pedicle screw extender from a second end portion thereof toward the first end portion thereof after the pedicle screw assembly is anchored within the bony structure and while the pedicle screw extender is engaged with the pedicle screw assembly. An operation can be performed for moving the blade body from adjacent the second end portion of the pedicle screw extender toward the first end portion thereof for positioning a first end portion of the blade body within tissue of the patient. An operation can be performed for engaging a retractor attachment structure at the second end portion of the blade body with a blade body mounting structure of a retractor after performing such moving.

In another embodiment of the present invention, a method for performing minimally invasive surgery can comprise a plurality of the following operations. An operation can be preformed for engaging a first end portion of a pedicle screw extender with a fixation rod receiving body of a pedicle screw assembly. The pedicle screw extender is engaged in a manner allowing simultaneous transfer of rotational torque applied thereto to a screw portion of the pedicle screw assembly and maintaining a longitudinal axis of the fixation rod receiving body in substantially coincidental alignment with a longitudinal axis of the screw portion. An operation can be performed for anchoring the pedicle screw assembly to a bony structure of a patient through a minimally invasive access opening in tissue at a surgery site. Such anchoring includes using the pedicle screw extender to apply rotational torque to the screw portion of the pedicle screw assembly. An operation can be performed for engaging a blade body with the pedicle screw extender at an exposed position above the tissue after the pedicle screw assembly is anchored within the bony structure and while the pedicle screw extender is engaged with the pedicle screw assembly. An operation can be performed for sliding the blade body from a second end portion of the pedicle screw extender toward the first end portion of the pedicle screw extender for positioning a first end portion of the blade body within the minimally invasive access opening in the tissue. An operation can be performed for disengaging the pedicle screw extender from the pedicle screw assembly. An operation can be performed for withdrawing the pedicle screw extender from within the minimally invasive access opening in said tissue after disengaging the pedicle screw assembly therefrom. Such withdrawing can include disengaging the pedicle screw extender from the blade body while the first end portion of the blade body remains within the minimally invasive access opening. An operation can be performed for engaging a retractor attachment structure at the second end portion of the blade body with a blade body mounting structure of a retractor after performing such withdrawing.

In another embodiment of the present invention, a method for performing surgery can comprise a plurality of the following operations. An operation can be performed for anchoring a first pedicle screw apparatus to a first bony structure of a patient and a second pedicle screw apparatus to a second bony structure of the patient. Each one of the pedicle screw assemblies includes a pedicle screw assembly having a first end portion of a pedicle screw extender attached thereto in a manner providing for simultaneous transfer of rotational torque applied thereto to a screw portion of the pedicle screw assembly and for maintaining a longitudinal axis of a fixation rod receiving body of the pedicle screw assembly in substantially coincidental alignment with a longitudinal axis of the screw portion. An operation can be performed for engaging a first blade body with the pedicle screw extender of the first pedicle screw assembly and a second blade body with the pedicle screw extender of the second pedicle screw assembly after performing such anchoring and while each one of the pedicle screw extends is engaged with the respective one of the pedicle screw assemblies. An operation can be performed for displacing each one of the blade bodies from a second end portion of the respective pedicle screw extender toward the first end portion thereof for positioning a first end portion of each one of the blade bodies within tissue of the patient adjacent the respective one of the bony structures. An operation can be performed for disengaging each one of the pedicle screw extenders from the respective one of the pedicle screw assemblies. An operation can be performed for engaging a retractor with both of the blade bodies after performing such displacing.

These and other objects, embodiments, advantages and/or distinctions of the present invention will become readily apparent upon further review of the following specification, associated drawings and appended claims.

BRIEF DESCRIPTION OF THE DRAWINGS

FIG. 12 is a partial fragmentary cross-sectional view showing a pedicle screw extender configured in accordance with the present invention engaged with a pedicle screw assembly, wherein an extension portion of the pedicle screw extender is engaged with a fixation rod receiving body of the pedicle screw assembly and a torque application member of the pedicle screw extender is disengaged from a bone screw of the pedicle screw assembly.

FIG. 13 is a partial fragmentary cross-sectional view of the pedicle screw extender shown in FIG. 12, wherein the extension portion of the pedicle screw extender is engaged with the fixation rod receiving body of the pedicle screw assembly and the torque application member of the pedicle screw extender is engaged from the bone screw of the pedicle screw assembly.

DETAILED DESCRIPTION OF THE DRAWING FIGURES

Figure 1:
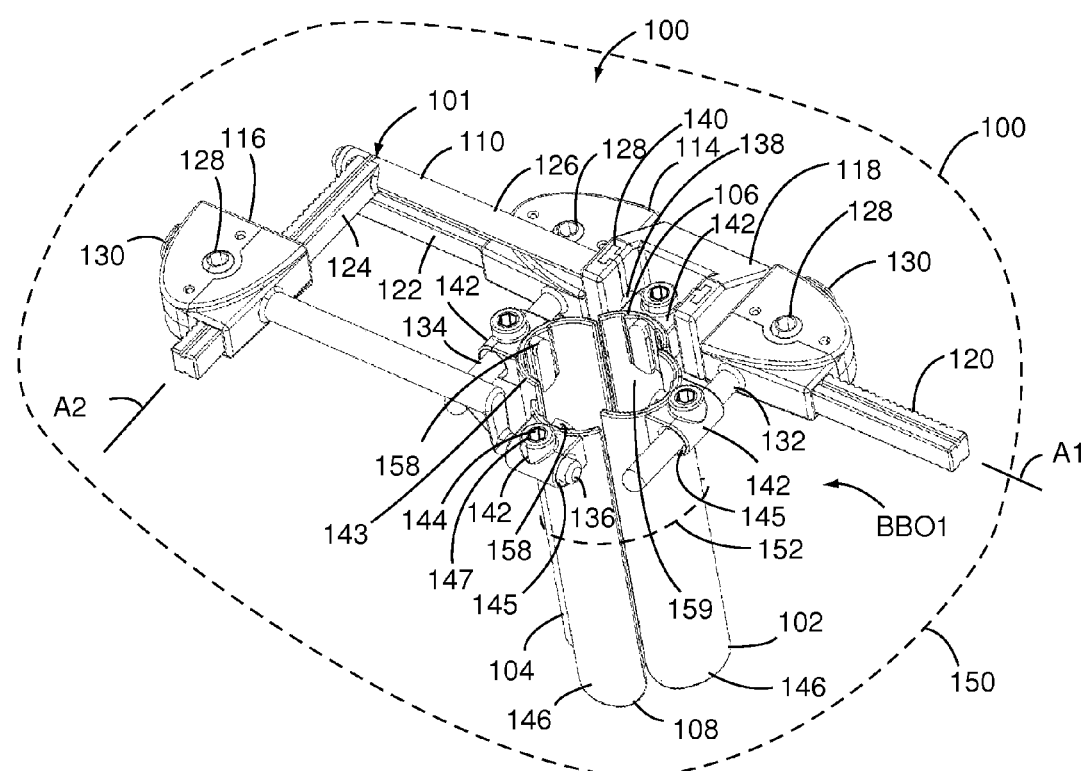
FIG. 1 is a perspective view showing a refractor apparatus configured in accordance with the present invention, wherein blade bodies thereof are in an adjacent orientation.

Referring to FIGS. 1-4, a retractor apparatus 100 configured in accordance with a first embodiment of the present invention is shown. The retractor apparatus 100 finds use in surgical procedures such as, for example, lumbar spine fusion surgery, lumbar diskectomy surgery and the like. The retractor apparatus 100 overcomes adverse issues associated with prior art approaches of placing pedicle screw assemblies through a retractor such as, for example, inadequate visualization of the pedicle using fluoroscopy through the retractor. The retractor apparatus 100 and associated surgical retractor component system are configured for allowing pedicle screw assemblies to be placed in a true percutaneous manner, thereby overcoming issues resulting from placing pedicle screw assemblies through a retractor.

The retractor apparatus 100 includes a refractor 101, a first blade body 102, a second blade body 104, a third blade body 106 and a fourth blade body 108. The retractor 101 includes a frame structure 110, a first blade translating unit 112, a second blade translating unit 114, and a third blade translating unit 116. A stationary blade mounting structure 118 of the frame structure 110 has a first blade translation unit mounting structure 120 and a second blade translation unit mounting structure 122 attached thereto. The first and second blade translation unit mounting structures 120, 122 extend in opposing directions from the stationary blade mounting structure 118 along a first reference axis A1. The first blade translating unit 112 is mounted on the first blade translation unit mounting structure 120 in a manner allowing the first blade translating unit 112 to be selectively translated along a length of the first blade translation unit mounting structure 120. Similarly, the second blade translating unit 114 is mounted on the second blade translation unit mounting structure 122 in a manner allowing the second blade translating unit 114 to be selectively translated along a length of the second blade translation unit mounting structure 122. Thus, a distance between the first and second blade bodies 102, 104 can be selectively varied.

A third blade translation unit mounting structure 124 is attached to the stationary blade mounting structure 118 through an extension member 126. The extension member 126 is configured for spacing the third blade translation unit mounting structure 124 away from (i.e., offsetting from) the stationary blade mounting structure 118. The third blade translation unit mounting structure 124 extends from the extension member 126 in a manner whereby it extends along a second reference axis A2. The second reference axis A2 extends substantially perpendicular to the first reference axis A1. The third blade translating unit 116 is mounted on the third blade translation unit mounting structure 124 in a manner allowing the third blade translating unit 116 to be selectively translated along a length of the third blade translation unit mounting structure 124, thereby allowing a distance between the third and fourth blade bodies 106, 108 to be varied. In this manner, the blade translation units mounting structure 112, 114 and 116 allow opposing ones of the blade bodies (102, 104, 106, 108) to be moved between an adjacent orientation BBO1 with resect to each other (FIG. 1) and a retracted orientation BBO2 with resect to each other (FIGS. 2-4).

It is disclosed herein that, in one embodiment, a blade translating unit being mounted on a blade translation unit mounting structure in a manner allowing the blade translating unit to be selectively translated along a length of the blade translation unit mounting structure includes the blade translation unit mounting structure having a surface feature (e.g., teeth) that are engaged by a mating structure (e.g., cog with teeth) of the blade translating unit. Preferably, a blade translating unit in accordance with the present invention includes a means for selectively inhibiting movement of the blade translating unit in at least one direction of travel thereof. For example, each one of the blade translating units (112, 114, 116) can include a movement causing device 128 and a movement inhibiting device 130. Rotation of the movement causing device 128 causes the respective one of the blade translating units (112, 114, 116) to move along the respective blade translation unit mounting structure in a first direction (e.g., away from the stationary blade mounting structure 118) and movement in the second direction is inhibited until the movement inhibiting device 130 of the same one of the blade translating units (112, 114, 116) is deactivated (i.e., manually depressed). In this manner, movement of each one of the blade translating units (112, 114, 116) along a length of the respective one of the blade translation unit mounting structures (120, 122, 124) in either direction can be selectively controlled.

Each one of the blade translating units (112, 114, 116) includes a respective blade body mounting structure (132, 134, 136) attached thereto. The blade body mounting structure 132 of the first blade translating unit 112 has the first blade body 102 mounted thereon. The blade body mounting structure 134 of the second blade translating unit 114 has the second blade body 104 mounted thereon. The blade body mounting structure 136 of the third blade translating unit 112 has the third blade body 106 mounted thereon. The stationary blade mounting structure 118 includes a blade body mounting structure 138 having the fourth blade body 108 detachably mounted within grooves 140 thereof. The first and second blade bodies 102, 104 are sometimes referred to as primary blade bodies. The third and fourth blade bodies 106, 108 are sometimes referred to as secondary blade bodies. The blade body mounting structures (132, 134, 136, 138) to which the blade bodies 102, 104, 106, 108) are attached are sometimes referred to by similar nomenclature (e.g., primary blade body mounting structure and secondary blade body mounting structure). The primary and the secondary blade bodies can be of different configuration (e.g., the primary blade bodies configured for angulation and secondary blade bodies not being configured for angulation).

As shown in FIGS. 1-4, a retractor attachment structure 142 of each one of the blade bodies (102, 104, 106, 108) is provided at a first end portion 143 of each one of the blade bodies (102, 104, 106, 108). The retractor attachment structure 142 of each one of the blade bodies (102, 104, 106, 108) is mounted on (i.e., engaged with) a respective one of the blade body mounting structures (132, 134, 136, 138) in a manner allowing angulation (i.e., rotation) thereabout and, optionally, translation therealong. Each retractor attachment structure 142 has a mounting structure receiving passage 145 extending therethrough and the engaged one of the blade body mounting structures (132, 134, 136, 138) is engaged within the mounting structure receiving passage 145 of a respective one of the blade bodies (102, 104, 106, 108), thereby allowing angulation and, optionally, translation of the respective one of the blade bodies (102, 104, 106, 108) relative to the engaged one of the blade body mounting structures (132, 134, 136, 138). It is disclosed herein, however, that one or more of the blade bodies (102, 104, 106, 108) can be engaged with the respective one of the blade body mounting structures (132, 134, 136, 138) in a manner that substantially inhibits angulation and/or translation of the respective one of the blade bodies (102, 104, 106, 108) relative to the engaged one of the blade body mounting structures (132, 134, 136, 138).

Each one of the blade bodies (102, 104, 106, 108) includes a respective blade securing device 144 engaged within a blade securing device passage 147. The blade securing device 144 of each one of the blade bodies (102, 104, 106, 108) is used for securing the respective one of the blade bodies (102, 104, 106, 108) in a fixed orientation (i.e., angulated and translated orientation) with respect to the engaged one of the blade body mounting structures (132, 134, 136, 138). In one embodiment (shown), the blade securing device 144 of each one of the blade bodies (102, 104, 106, 108) is a setscrew, pin, or other suitable type of fastener or device. The blade securing device 144 is selectively movable between a first position (e.g., untightened) for allowing the respective one of the blade bodies (102, 104, 106, 108) to be pivoted about and translated along the engaged one of the blade body mounting structures (132, 134, 136, 138) and a second position (e.g., tightened) for substantially inhibiting movement of the respective one of the blade bodies (102, 104, 106, 108) with the engaged one of the blade body mounting structures (132, 134, 136, 138). An elongated tool engagable with the blade securing device 144 (e.g., a hex screw driver or the like) can be used to both move the blade securing device 144 between its first position (e.g., untightened) and its second position (e.g., tightened) and to set a desired orientation of the respective one of the blade bodies (102, 104, 106, 108) when the blade securing device 144 is in its first position. It is disclosed herein that that the present invention is not limited to any particular type or configuration of means for securing the respective one of the blade bodies (102, 104, 106, 108) in a fixed orientation (i.e., angulated and translated orientation) with respect to the engaged one of the blade body mounting structures (132, 134, 136, 138).

The blade body mounting structures 132, 134 of the first and second blade translating units 112, 114 are jointly configured such that the first blade body 102 and the second blade body 104 are in opposed facing relationship to each other. Similarly, the blade body mounting structures 136, 138 of the first and second blade translating units 116, 118 are jointly configured such that the third blade body 106 and the fourth blade body 108 are in opposed facing relationship to each other. As shown, in one embodiment of the present invention, the blade body mounting structures 132, 134 of the first and second blade translating units 112, 114, respectively, extend substantially parallel with the second reference axis A2 and the blade body mounting structures 136, 138 of the third and fourth blade translating unit 116 and the stationary blade mounting structure 118, respectively, extend substantially parallel with the first reference axis A1.

Preferably, but not necessarily, all of the blade bodies (102, 104, 106, 108) of the retractor apparatus 100 are identical (i.e., as shown in FIGS. 1-4). However, it is disclosed herein that blade bodies of a retractor apparatus in accordance with the present invention need not be identical. For example, in an alternate embodiment, only blade bodies that are in opposed facing relationship to each other are the same as each other. It is disclosed herein that each one of the blade bodies (102, 104, 106, 108) is an example of a retractor-mounted implement in accordance with the present invention. Other examples of such a refractor-mounted implement include, but are not limited to, an ancillary component mounting structure, a lighting device, a suction device, a positioning device, a clamping device and the like. Such retractor-mounted implement are configured for being engaged with the blade mounting structure in the same manner as the blade bodies (102, 104, 106, 108).

Figure 2:
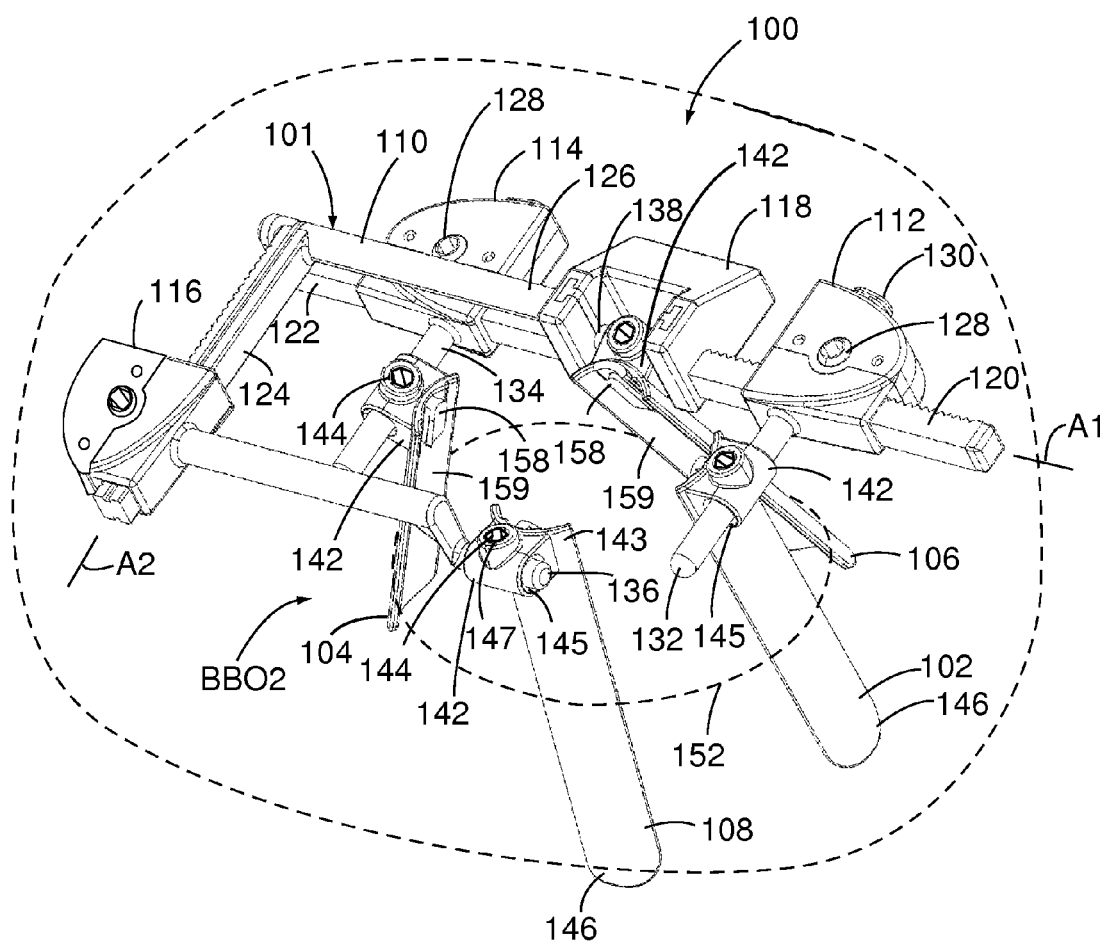
FIG. 2 is a perspective view of the retractor apparatus shown in FIG. 1, wherein the blade bodies are in a retracted orientation.
Figure 3:
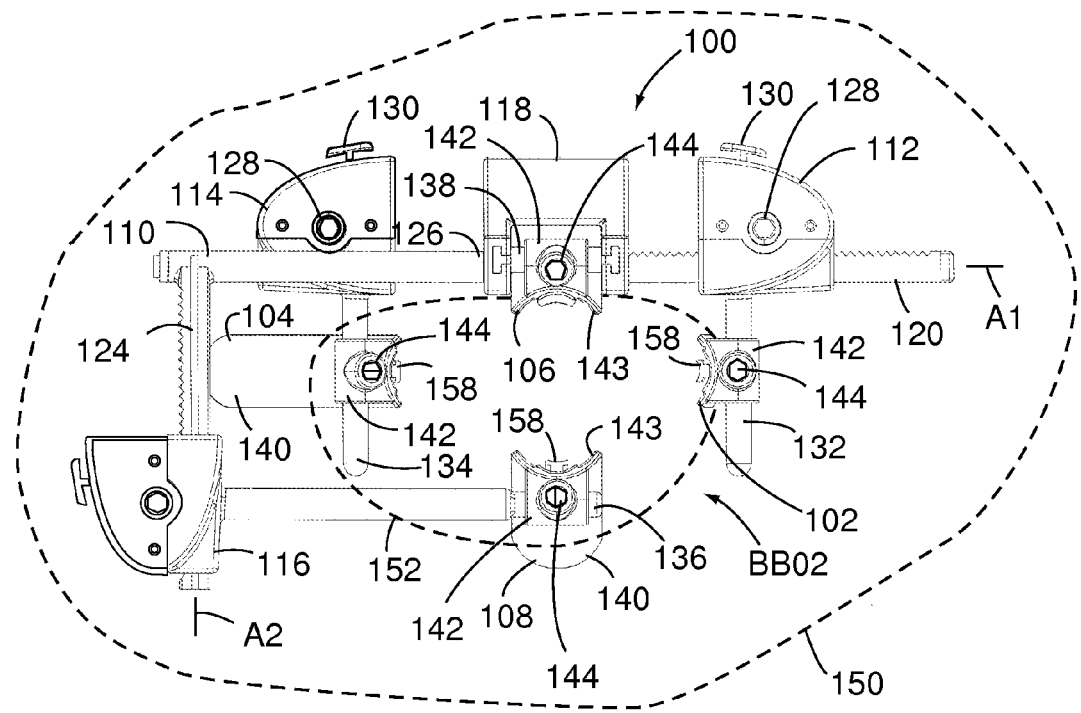
FIG. 3 is a top of the retractor apparatus shown in FIG. 1, wherein the blade bodies are in a retracted orientation.
Figure 4:
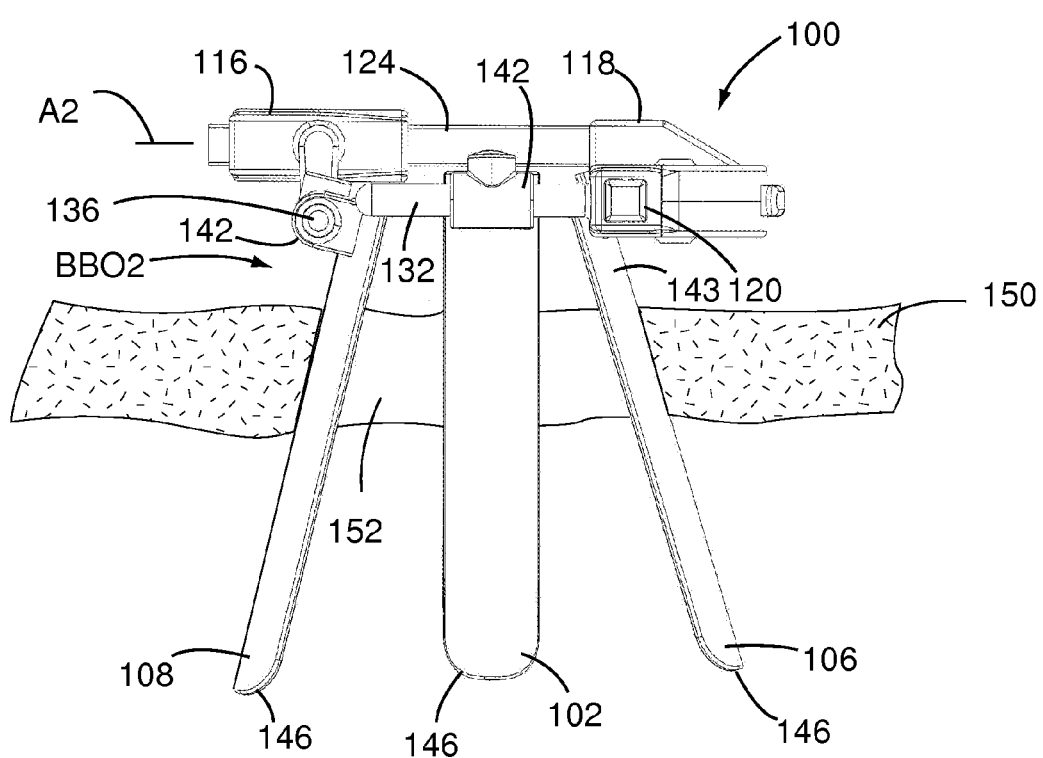
FIG. 4 is a side view of the retractor apparatus shown in FIG. 1, wherein the blade bodies are in a retracted orientation.

Still referring to FIGS. 1-4, it can be seen that the retractor apparatus 100 can be used in a minimally invasive surgical procedure. As shown in FIG. 1, the retractor apparatus 100 is positioned above a minimally invasive opening 150 within tissue 152 of a patient, with the blade bodies (102, 104, 106, 108) in an adjacent orientation BBO1 with a respective second end portion 146 (i.e., a tip portion) thereof extending through the minimally invasive opening 150. As shown in FIGS. 2-4, the blade bodies ((102, 104, 106, 108) can be moved to a retracted orientation BBO2 through manipulation of the blade translating units (112, 114, 116). Furthermore, through manipulation of the securing device 142 of each one of the blade body mounting structures (132, 134, 136, 138), angulation of the blade bodies (102, 104, 106, 108) can be independently adjusted as necessary or desirable. Such angulation is useful in that it allows portions of the tissue 150 within the minimally invasive opening 150 to be pushed back further than portions of the tissue 150 at an entrance to the minimally invasive opening 150. Accordingly, it can be seen that the retractor apparatus 100 advantageously allows the tissue 152 to be retracted for sufficiently expanding the size of the minimally invasive opening 150 to allow structures below the tissue 152 (e.g., vertebrae, bones, organs, etc) to be accessed.

An alignment member 158 protrudes from an interior surface 159 of each one of the blade bodies (102, 104, 106, 108). As will be discussed below in greater detail, the alignment member 158 is engagable within a mating slot or channel of a pedicle screw extender 240 (shown in FIGS. 8-10) for limiting unrestricted rotation of an engaged one of the blade bodies (102, 104, 106, 108) about an extension portion 242 of the pedicle screw extender 240. The alignment member 158 and the mating slot or channel 244 of the pedicle screw extender 240 are jointly configured for allowing the engaged one of the blade bodies (102, 104, 106, 108) to be slide along at least a portion of a length of the extension portion 242 of the pedicle screw extender 240.

It is disclosed herein that the alignment member 158 of one or more of the blade bodies (102, 104, 106, 108) can be used for purposes in addition to being engaged within the mating slot or channel of the pedicle screw extender 240. For example, the alignment member 158 of one or more of the blade bodies (102, 104, 106, 108) can also be used as an attachment point for an external light source to help a surgeon with improve vision into an invasive site. In view of the disclosures made herein, a skilled person will appreciate other uses for the alignment member 158 of one or more of the blade bodies (102, 104, 106, 108).

As shown, the second end portion 146 of each one of the blade bodies (102, 104, 106, 108) is smoothly curved (i.e., radiused). However, for certain procedures and/or uses, a skilled person will appreciate that the second end portion can be configured in a different manner. Foe example, for some procedures and/or uses, the second end portion 146 can be configured for being anchored within a bony structure. For such procedures and/or uses that require anchoring, the second end portion 146 can be serrated, sharply pointed, or otherwise suitably configured to allow for such anchoring.

Preferably, but not necessarily, all or a portion of the components of the retractor 101 are made from a fluoro-transparent or fluoro-translucent material. In at least one embodiment of the present invention, the retractor 101 is used in a surgical procedure where the retractor 101 will be installed on a patient during fluoroscopy of the patient. A skilled person will be well aware of suitable surgical grade materials and/or engineering grade materials that are fluoro-transparent or fluoro-translucent material. Depending on the specific application, a skilled person will also appreciate that all or a portion of the components of the retractor 101 can be made from materials such as stainless steel, carbon fiber, PEEK, titanium, or other such well known materials from which surgical implements are and can be made.

Figure 5:
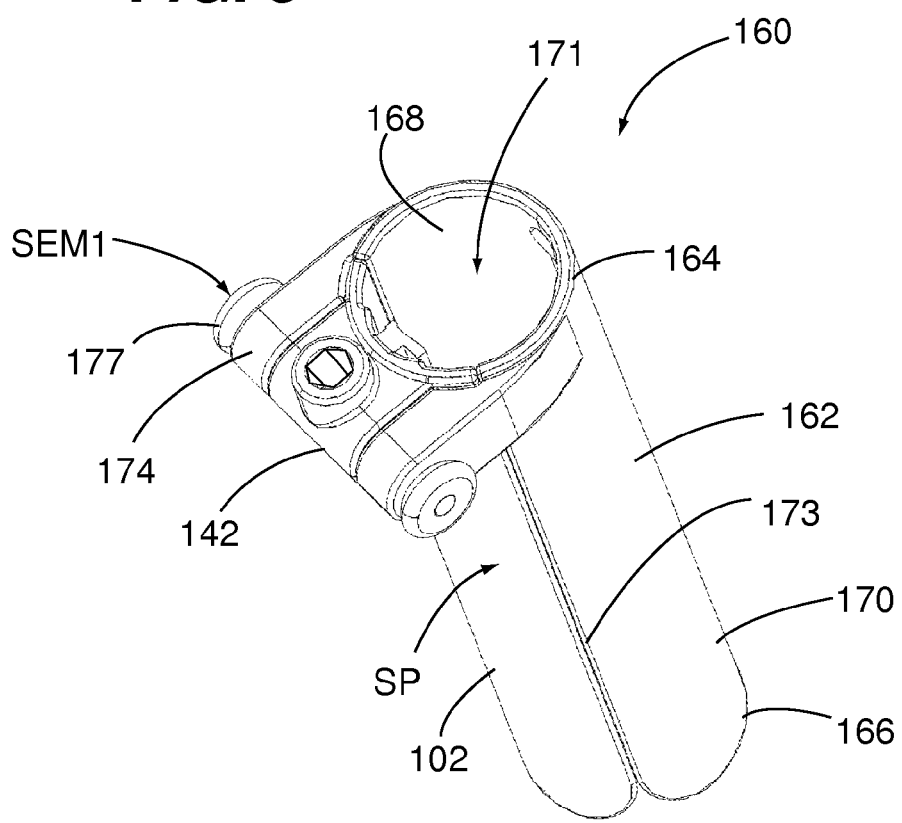
FIG. 5 is a perspective view of a blade body assembly configured in accordance with the present invention, wherein a blade body of the blade body assembly is in a seated position with respect to a blade body surround of the blade body assembly.
Figure 6:
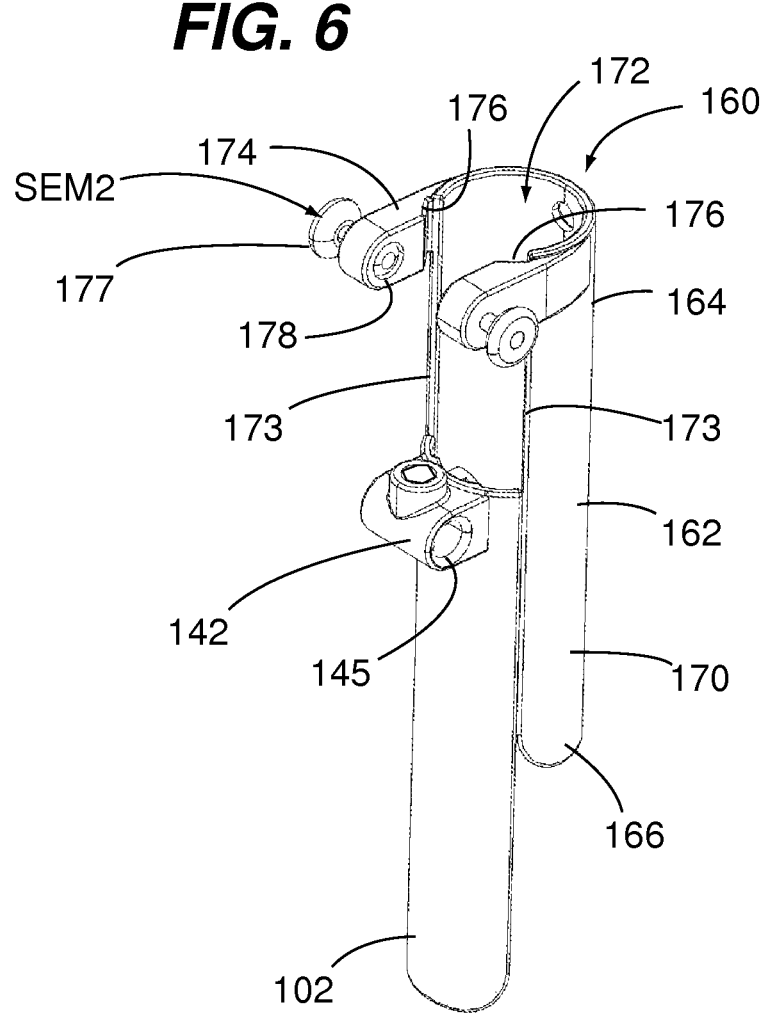
FIG. 6 is a perspective view of the blade body assembly shown in FIG. 5, wherein the blade body surround is in a displaced position with respect to the blade body.

Referring now to FIGS. 5 and 6, a blade body assembly 160 in accordance with an embodiment of the present invention is shown. The blade body assembly 160 includes the first blade body 102 (i.e., the blade body 102) discussed above in reference to FIGS. 1-4 and a blade body surround 162. While the blade body shown in FIGS. 5 and 6 is the first blade body 102 of FIGS. 1-4, it is disclosed herein that a blade body of the blade assembly 160 can be any blade body suitably configured for use with the blade surround 162. Accordingly, any of the of the blade bodies (102, 104, 106, 108) discussed above in reference to FIGS. 1-4 can be used in combination with the blade surround 162.

The blade body surround 162 has a first end portion 164, a second end portion 166, an interior surface 168 and an exterior surface 170. The blade surround 162 has a slot 172 extending through the first end portion 164 and the second end portion 166. It is disclosed herein that the slot 172 can extend through the first and second end portions 168, 170 or through the first end portion 164 and end adjacent to or at the second end portion 166. The blade body 102 and the blade body surround 162 are jointly configured to form a generally cylindrical-shaped structure when the blade body 102 is in a seated position SP within the slot 172. This cylindrical structure defines a central passage 171 (FIG. 5) of the blade body assembly 160 that extends between the first and second end portions 164, 166 of the blade body surround 162. Preferably, but not necessarily, edge portions 173 of the slot 172 abut side edges of the blade body 102 when the blade body 102 is in the seated position SP within the slot 172.

The blade body surround 162 includes spaced apart blade attachment bosses 174 at its first end portion 164. The spaced apart blade attachment bosses 174 are one example of a blade body attachment structure 174. The slot 172 intersects each one of the spaced apart blade attachment bosses 174 in a manner providing recesses 176 in each one of the spaced apart blade attachment bosses 174. The recess 176 of each one of the spaced apart blade attachment bosses 174 has a mating portion of the blade body 102 residing therein when the blade body 102 is in the seated position SP within the slot 172. Preferably, the recesses 176, the edge portions 173 of the slot 172, and the blade body 102 are jointly configured such that engagement of the blade body 102 within the recesses 176 substantially constrains movement of the blade body 102 relative to the blade body surround 162 to being along a length of the slot 172.

The retractor attachment structure 142 of the blade body 102 is positioned between the spaced apart blade attachment bosses 174 when the blade body 102 is in the seated position SP within the slot 172. Each one of the spaced apart blade attachment bosses 174 has a surround engagement member 177 slideably mounted with a surround engagement member receiving passage 178. The surround engagement member receiving passage 178 is aligned with the mounting structure receiving passage 145 of the retractor attachment structure 142 when the blade body 102 is in the seated position SP within the slot 172. Each surround engagement member 177 the blade body mounting structure is selectively movable between an engaged position SEM1 and a disengaged position SEM2. Each surround engagement member 177 is of a sufficient length for allowing simultaneous engagement within the respective surround engagement member receiving passage 178 and the mounting structure receiving passage 145 of the blade body 102 when in its engaged position SEM1 with the blade body 102 is in the seated position SP within the slot 172. In this manner, one or both of the surround engagement members 177 can limit displacement of the blade body 102 with respect to the blade body surround 162 when engaged within the mounting structure receiving passage 145 of the blade body 102.

Figure 7:
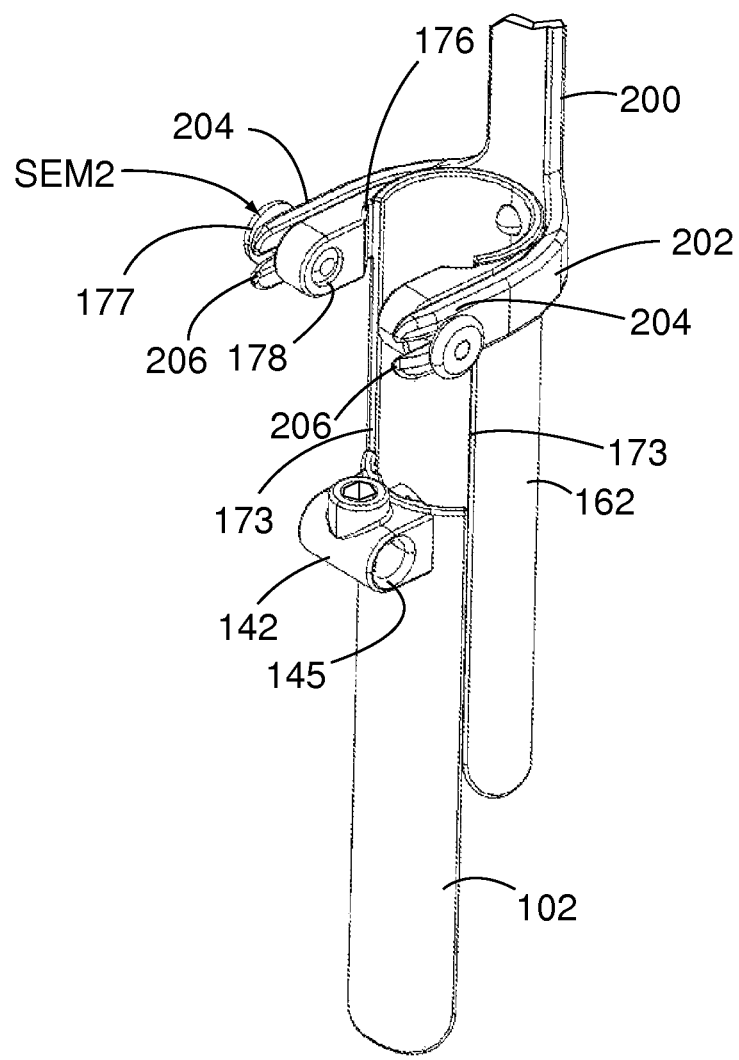
FIG. 7 is a perspective view of the blade body assembly shown in FIG. 5, wherein a separation tool is attached to the blade body surround.

As shown in FIG. 7, a surround separating tool 200 is engagable with the blade body surround 162 for disengaging the surround engagement members 177 and separating the blade body surround 162 from the blade body 102. The surround separating tool 200 includes a head portion 202 that includes spaced apart engagement member retractors 204. Each one of the spaced apart engagement member retractors 204 has a slotted tip portion 206. The engagement member retractors 204 are spaced apart such that the blade body surround 162 can be positioned therebetween with one of the blade attachment bosses 174 inboard of each one of the engagement member retractors 204. When engaging the head portion 202 with the blade body surround, the slotted tip portion 206 of each spaced apart engagement member retractor 204 slides between the adjacent surround engagement member 177 and adjacent blade attachment boss 174, thereby moving the surround engagement member 177 from its engaged position SEM1 (see FIG. 5) to its disengaged position SEM2. With each surround engagement member 177 in its disengaged position SEM2, the blade body surround 162 can be slid out of engagement with the blade body 102 by pulling on the surround separating tool 200 in a direction generally parallel with the slot edge portions 173.

Figure 8:
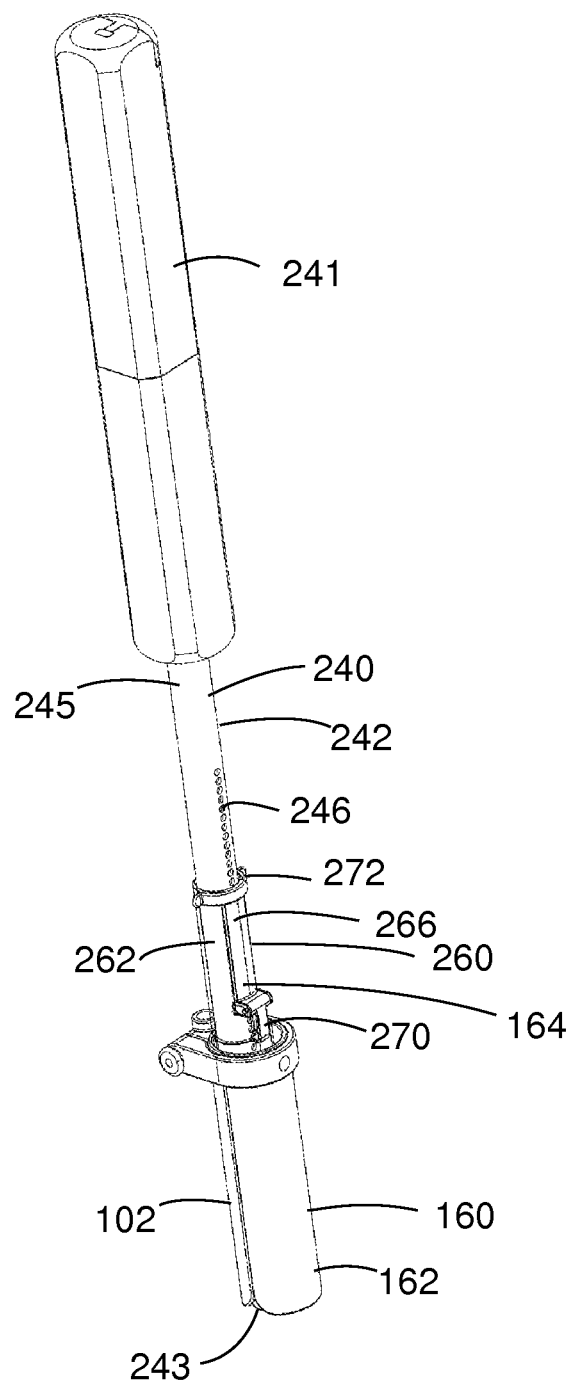
FIG. 8 is a perspective view showing a pedicle screw extender assembly configured in accordance with the present invention.
Figure 9:
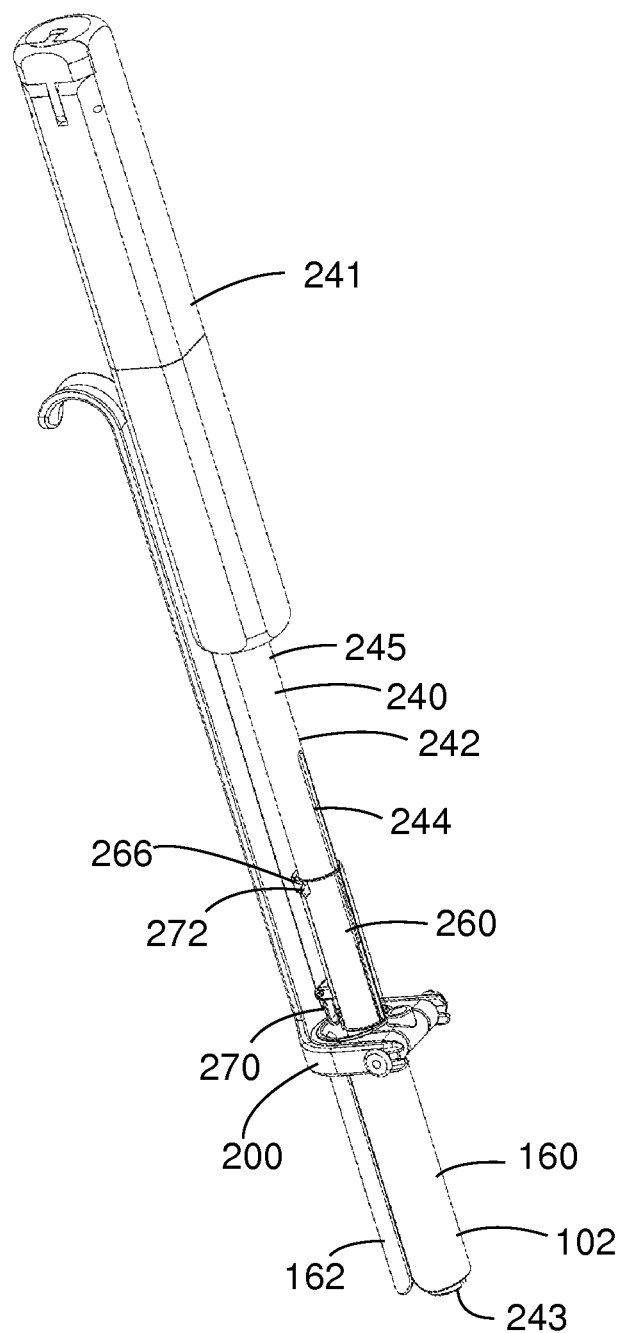
FIG. 9 is a perspective view of the pedicle screw extender assembly shown in FIG. 8, wherein a separation tool is engaged with a blade body surround of the pedicle screw extender assembly.
Figure 10:
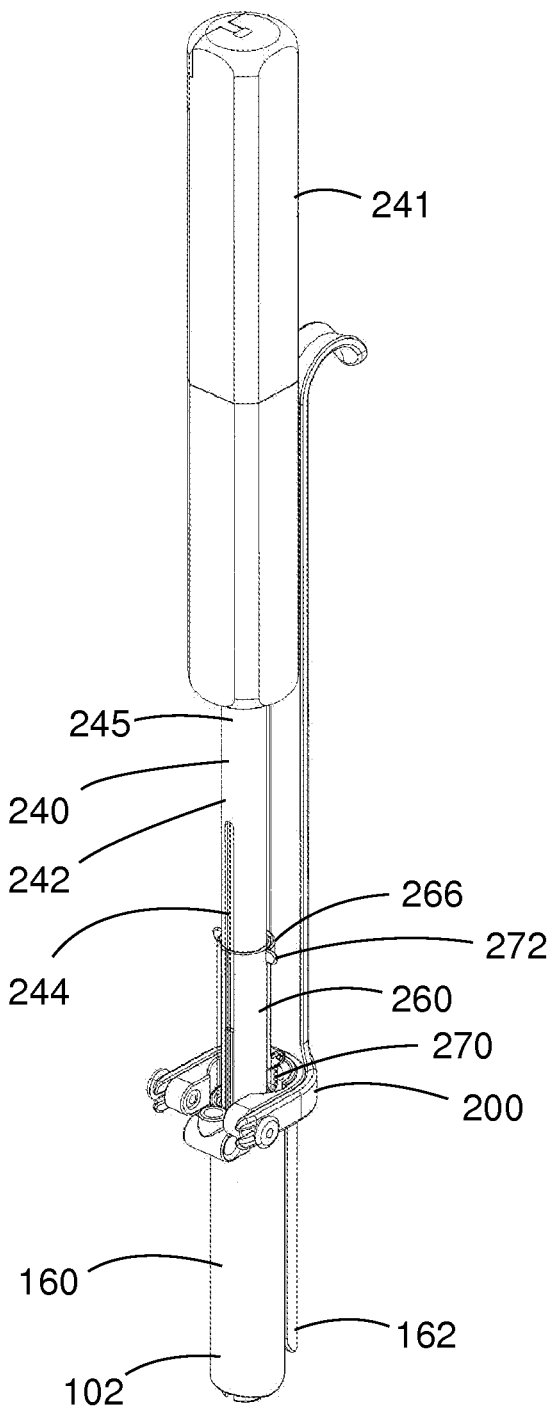
FIG. 10 is a perspective view of the pedicle screw extender assembly shown in FIG. 8, wherein the blade body surround is in a displaced position with respect to the blade body.

FIGS. 8-10 shown various interactions between the blade body assembly 160, the surround separation tool 200, the pedicle screw extender 240, and a blade assembly retainer 260. The pedicle screw extender 240 includes a handle portion 241 and an extension portion 242. The extension portion 242 includes a first end portion 243 and a second end portion 245. The handle portion 241 is attached to the second end portion 245 of the extension portion 242 in a manner allow torsional force resulting from twisting of the handle portion 241 to be exerted on the extension portion 242.

The extension portion 242 of the pedicle screw extender 240 is configured for carrying the blade body assembly 160 during installation of a pedicle screw within a bony structure of a patient. The alignment member 158 (see FIGS. 1-4) of the blade body 102 is engaged within the mating channel 244 of the extension portion 242 of the pedicle screw extender 240. The channel 244 extends from the first end portion 243 of the extension portion 242 toward its first end portion 243. In this manner, the blade body 102 limits unrestricted rotation of the blade body assembly 160 about the extension portion 242 of the pedicle screw extender 240 while allowing the blade body assembly 160 to be slide along at least a portion of a length of the extension portion 242 of the pedicle screw extender 240. In one embodiment, the alignment member 158 has a cross-sectional shape (e.g., t-shaped) that causes the alignment member 158 to be engaged within the mating channel 244. In this manner, the alignment member 158 and the mating channel 244 of the extension portion 242 are jointly configured such that, once engaged with the mating channel 244, the alignment member 158 is constrained within the mating channel 244 in a manner allowing it to only slide therealong.

Figure 11:
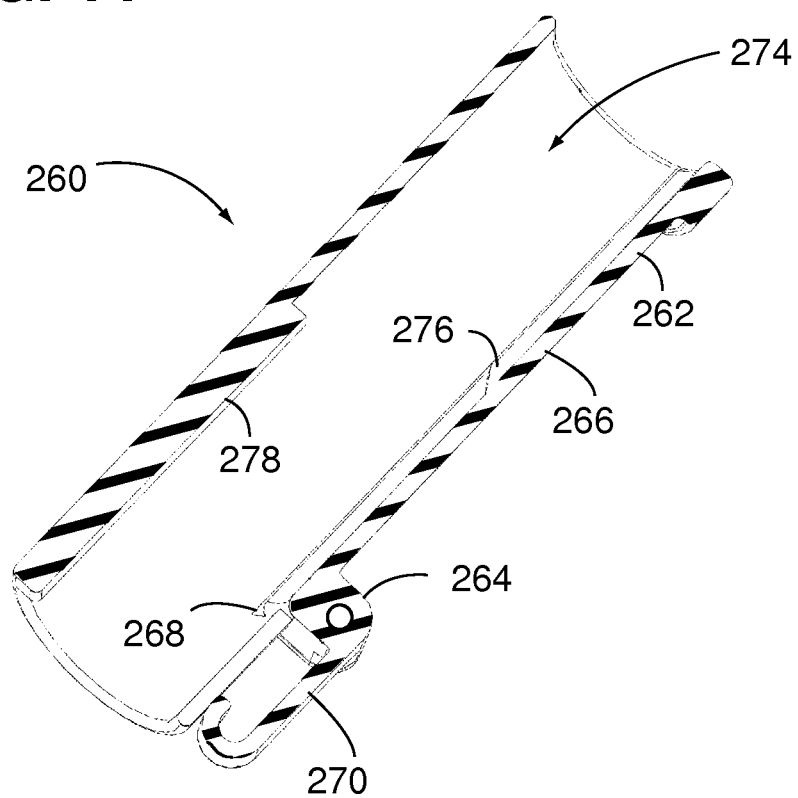
FIG. 11 is a cross-sectional view of a blade body retainer of the pedicle screw extender assembly shown in FIGS. 8-10.

Referring to FIG. 11, the blade assembly retainer 260 is configured for being engaged with the extension portion 242 of the pedicle screw extender 240 in a manner that limits unrestricted movement of the blade body assembly 160 along the length of the extension portion 242 of the pedicle screw extender 240. The blade assembly retainer 260 includes a generally cylindrical retainer body 262 and an extension engagement member 264. The extension engagement member 264 is pivotably mounted on the retainer body with a first end portion 266 of the extension engagement member 264 disposed within a slot 268 of the body retainer 262 and a second end portion 270 engaged with an exterior surface of the retainer body 262. The second end portion 270 serves as a cantilever spring for urging the first end portion inward such that an arm 272 attached to the second end portion 270 of the extension engagement member 264 bears against the exterior surface of the retainer body 262. In this manner, the first end portion 266 is inwardly biased with respect to a central passage 274 of the blade assembly retainer 260. The first end portion 266 can be outwardly displaced through application of force on the arm 272. The first end portion 266 of the extension engagement member 264 includes a protrusion 276. The protrusion 276 extends inwardly toward the central passage 274 of the blade assembly retainer 260. As is discussed below in greater detail, the protrusion 276 is engageable with a mating feature of the extension portion 242 of the pedicle screw extender 240 for securing the blade assembly retainer 260 in a fixed position on the extension portion 242 of the pedicle screw extender 240. Protrusion 278 is engageable with the channel 244 of the extension portion 242 for limiting unrestricted rotation of the blade assembly retainer 260 about the extension portion 242 and maintaining alignment of the protrusion 276 with the a mating feature of the extension portion 242 (e.g., spaced apart apertures 246 shown in FIG. 8).

Referring to FIGS. 8-10, in preparation for installation of a pedicle screw assembly using the pedicle screw extender 240, the blade assembly retainer 260 is mounted on the extension portion 242 of the pedicle screw extender 240. The protrusion 276 of the blade assembly retainer 260 is engaged with one of a plurality of spaced apart apertures 246 within the extension portion 242 of the pedicle screw extender 240, thereby securing the blade assembly retainer 260 in a fixed position along the length of the extension portion 242 of the pedicle screw extender 240. The blade body assembly 160 is then slid onto the extension portion 242 of the pedicle screw extender 240 with the alignment member 158 of the blade body 102 engaged within the mating channel 244 of the extension portion 242 of the pedicle screw extender 240. The degree to which the blade body assembly 160 can be slid onto the extension portion 242 of the pedicle screw extender 240 will thus be dictated by placement of the blade assembly retainer 260. As shown in FIGS. 9 and 10, engagement of the surround separation tool 200 with the blade body assembly 160 as discussed in detail in reference to FIG. 7 provides for separation of the blade body surround 162 from the blade body 102 while leaving the blade body still engaged with the extension portion 242 of the pedicle screw extender 240. Such separation of the blade body surround 162 from the blade body 102 allows for the blade body 102 to be engaged with a blade body mounting structure of a retractor apparatus (e.g., one of the one of the blade body mounting structures (132, 134, 136, 138) of the retractor apparatus 100 discussed above in reference to FIGS. 1-4). This assembly of the blade body assembly 160, the surround separation tool 200, the pedicle screw extender 240, and a blade assembly retainer 260 is referred to herein as a pedicle screw extender assembly.

Referring now to FIGS. 12 and 13, an embodiment of a structure for engagement of the pedicle screw extender 240 with a pedicle screw assembly 280 is discussed. In view of the disclosures made herein, a skilled person will appreciate other embodiments for accomplishing such engagement. Thus, the present invention is not unnecessarily limited to any particular structure for engagement of a pedicle screw extender in accordance with the present invention with a pedicle screw assembly.

The first end portion 243 of the extension portion 242 of the pedicle screw extender 240 is configured for having the pedicle screw assembly 280 engaged therewith. The first end portion 243 is configured for transferring rotational torque applied to the elongated extension portion 242 via the handle 242 (FIGS. 8-10) to a bone screw 282 (i.e., a screw portion) of the pedicle screw assembly 280 while simultaneously maintaining a longitudinal axis A3 of a fixation rod receiving body 284 of the pedicle screw assembly 280 in coincidental alignment with a longitudinal axis A4 of the bone screw 282.

As shown in FIG. 12, a body engagement member 247 extends from an interior surface 249 of the extension portion 242 at its first end portion 243. The body engagement member 247 is engaged with a mating feature 286 (e.g., threads) on an exterior surface 288 of the fixation rod receiving body 284 of the pedicle screw assembly 280. Through such engagement of the body engagement member 247 with the mating feature 286 of the fixation rod receiving body 284 of the pedicle screw assembly 280, a longitudinal axis A5 of the extension portion 242 of the pedicle screw extender 240 is held in substantial alignment with the longitudinal axis A3 of the fixation rod receiving body 284 of the pedicle screw assembly 280.

A torque application member 251 of the pedicle screw extender 240 is slideable mounted within a central passage (i.e., defined by the interior surface 249) of the extension portion 242. The torque application member 251 is slideable between a disengaged position TAM1 (FIG. 12) and an engaged position TAM2 (FIG. 13). For example, sliding of the torque application member 251 can implemented via a movement control mechanism mounted on/within the handle 241. The torque application member 251 is engaged with the extension portion 242 and/or the handle 241 in a manner allowing torque applied to the handle 241 to be at least partially, if not fully, exerted on the torque application member 251. Examples of means for allowing such torque transmission between the handle and the torque application member 251 include, but are not limited to, a splined interface, non-round interface or the like.

When the torque application member 251 is in its disengaged position TAM1, a tip portion 253 of the torque application member 251 is disengaged from within a torque application portion 290 of the bone screw 282 and a rod saddle engaging portion 255 of the torque application member 251 is disengaged from within a rod receiving saddle 292 of the fixation rod receiving body 284, as is shown in FIG. 12. The body engagement member 247 can be readily engaged with the mating feature 286 of the fixation rod receiving body 284 of the pedicle screw assembly 280 when the torque application member 251 is in its disengaged position TAM1. A recessed structure configured for receiving a flat tip driver, a star/cross driver, a hex driver, or the like is an example of the torque application portion 290 of the bone screw 282. When the torque application member 251 is in its engaged position TAM2, the tip portion 253 of the torque application member 251 is engaged within the torque application portion 290 of the bone screw 282 and the rod saddle engaging portion 255 of the torque application member 251 is engaged within the rod receiving saddle 292 of the fixation rod receiving body 284. The rod saddle engaging portion 255 and the rod receiving saddle 292 are jointly configured to preclude relative rotational movement therebetween when the rod saddle engaging portion 255 is engaged within the rod receiving saddle 292, thereby securing the pedicle screw assembly 280 to the pedicle screw extender 240 while the torque application member 251 is in its engaged position TAM2. Through engagement of the torque application member 251 with the torque application portion 290 of the bone screw 282, the longitudinal axis A5 of the extension portion 242 of the pedicle screw extender 240 is held in substantial alignment with the longitudinal axis A4 of the bone screw 282. Furthermore, the present invention is advantageously not unnecessarily limited to use with a particular type, brand or configuration of pedicle screw assembly as the first end portion 243 of the extension portion 242 of the pedicle screw extender 240 can be configured for use with a particular pedicle screw assembly.

Figure 14:
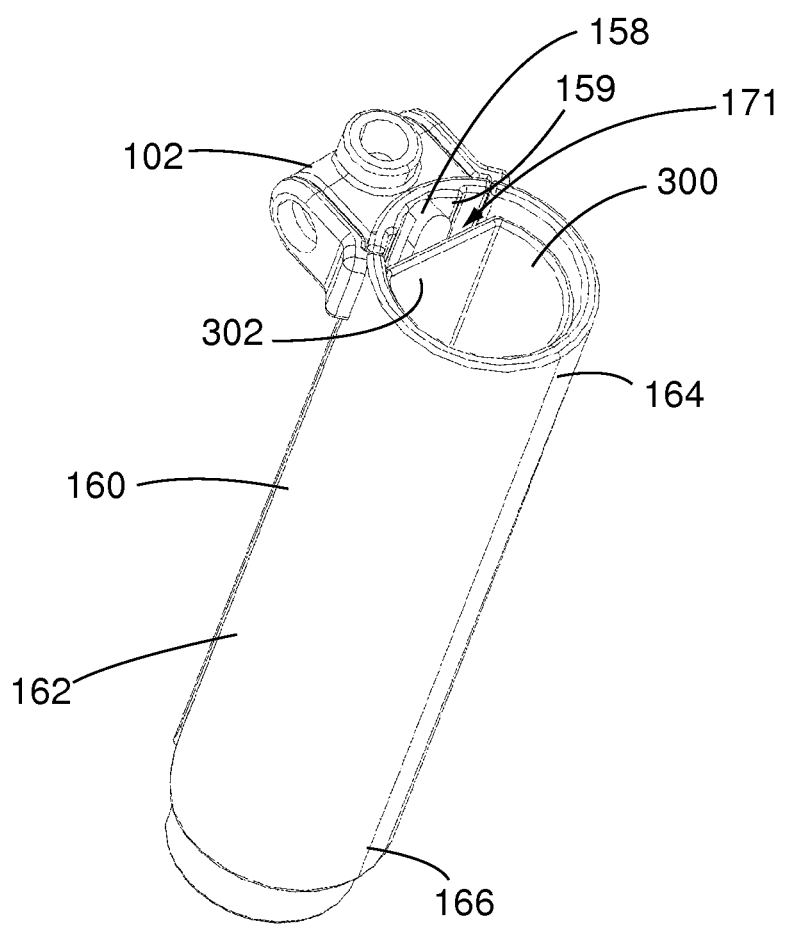
FIG. 14 is a perspective view showing a tissue dilatator configured in accordance with the present invention, wherein the tissue dilator is engaged with a blade body assembly configured in accordance with the present invention.

FIG. 14 shows a tissue dilatator 300 configured specifically for use with the blade body assembly 160. As discussed above, the blade body 102 and the blade body surround 162 are jointly configured to form a generally cylindrical-shaped structure when the blade body 102 is in a seated position within the slot 172 (FIG. 6) of the blade body surround 162. This cylindrical structure defines a central passage 171 (FIG. 5) of the blade body assembly 160 that extends between the first and second end portions 164, 166 of the blade body surround 162. Also discussed above, the blade body 102 has an alignment member 158 that protrudes from its interior surface 159. As such, the tissue dilator 300 has a D-shaped cross sectional profile to accommodate the alignment member 158 (i.e., a flat sidewall 302 of the tissue dilator 300 provides clearance for the alignment member 158).

The tissue dilator 300 is one of a series of dilators used with the blade body assembly 160. Preferably, all of the dilators have the same cross-sectional shape as the dilator 300. The dilator 300 is the largest, with the next smaller size dilator being sized to be slideably engaged within the dilator 300 in a close tolerance manner. Similarly, each dilator of the series is similarly sized to fit within the next larger size dilator.

Discussed now is a method of using the surgical retractor system components discussed above in a lumbar spine fusion surgical procedure. A lumbar spine fusion surgical procedure is one example of the many surgical procedure where surgical retractor system components in accordance with the present invention will find applicability. In view of the inventive disclosures made herein, a skilled person will appreciate other known and yet to be discovered surgical procedures in which surgical retractor system components in accordance with the present invention will find applicability.

An overall method of using such surgical retractor system components in a lumbar spine fusion surgical procedure includes the following operations (i.e., steps). A K-wire is installed through tissue of a patient into a bony structure into which a pedicle screw assembly is to be placed. After the K-wire is installed, a series of tissue dilators (i.e., those discussed above in reference to the tissue dilator 300) are installed over the K-wire, thereby dilating soft tissue of the patient. Next, a first pedicle screw assembly is engaged with a first pedicle screw extender assembly configured in accordance with an embodiment of the present invention (i.e., the pedicle screw extender 240 having the blade assembly 160 and the blade assembly retainer 260 mounted thereon as discussed above in reference to FIGS. 8-13). The pedicle screw assembly can be any suitable cannulated pedicle screw assembly such as those that are currently commercially available from numerous manufacturers. The pedicle screw extender 240 will be configured for use with a corresponding pedicle screw assembly.

The first pedicle screw assembly is then driven into the required bony structure of a patient (e.g., a vertebrae) through the largest one of the tissue dilators (i.e., smaller tissue dilators removed as necessary). It is disclosed herein that the pedicle screw assembly and the pedicle screw extender 240 are preferably cannulated for allowing placement over the k-wire. The pedicle screw extender assembly remains attached to the respective pedicle screw assembly at this point in the method. The operations performed thus far for installing the first pedicle screw assembly are then repeated for at least a second pedicle screw assembly (i.e., a pair of installed pedicle screw assemblies in spaced apart relationship, with each pedicle screw assembly being installed with a respective pedicle screw extender assembly). For example, a first pedicle screw assembly can be installed in a first vertebrae and the second pedicle screw assembly can be installed in a second vertebrae.

Next, the surround separation tool 200 discussed above in reference to FIGS. 8-10 is used for separating the blade body surround 162 from each blade body assembly 160. The blade body surround 162 and the blade body surround separation tool 200 are removed from within the dilator 300. As discussed above, the blade body of each blade body assembly (i.e., the blade body 102, 104) remain engaged with the respective pedicle screw extender 240 even after the blade body surround 162 is removed from each one of the blade body assemblies 160.

At this point in the method, the largest dilator (i.e., dilator 300) is still in place within tissue at a surgical site of the patient, two pedicle screw assemblies are installed within respective bony structure of the patient, and each one of the pedicle screw assemblies has a respective pedicle screw extender 240 attached thereto. Each pedicle screw extender 240 has a respective blade body (102, 104) attached thereto and is extending through a respective dilator.

The blade body on each pedicle screw extender 240 is now slid downward into the dilator such that an upper end portion of the blade body is above the tissue of the patient and a lower end portion of each blade body is below a surface of the tissue (i.e., is within a minimally invasive surgical site of the patient). A retractor attachment structure 142 of each one of the blade bodies 102, 104 is attached to a respective blade body mounting structure (i.e., blade body mounting structure 132 and blade body mounting structure 134) of the retractor 101. Preferably, but not necessarily, the refractor 101 is fixedly attached to an articulating arm of an operating table. For example, the stationary blade mounting structure 118 of the retractor 101 can have an integral mounting structure configured for being attached to a fixed body such as, for example, the operating table or a floor-mounted structure.

With the blade bodies 102, 104 attached to the blade body mounting structures 132, 134 of the retractor 101, angulation of each one of the blade bodies 102, 104 can set through use of the blade securing device 144 thereof and a suitable tool (e.g., a hex driver). The pedicle screw extender 240, including the respective blade assembly retainer 260, is then detached from each one of the pedicle screw assemblies and is removed from within the dilator 300. The dilator 300 and K-wire are now removed and the tissue is retracted accordingly through use of the first and/or second blade translating units 112, 114 of the retractor 101. During such retraction, angulation of one or both of the blade bodies 102, 104 can be adjusted. If required and/or desired, a retractor attachment structure 142 of two secondary blade bodies (e.g., blade bodies 106, 108) can be attached to respective secondary the blade body mounting structures (e.g., the third blade body mounting structure 136 and the fourth blade body mounting structure 138) of the retractor 101 and refracted accordingly through use of a respective blade translating unit (e.g., the third blade translating unit 116) of the retractor 101.

As can be gathered from the foregoing discussions and disclosures, a retractor apparatus and associated surgical retractor system components configured in accordance with the present invention advantageously allow retractor placement over a pedicle screw assembly/pedicle screw extender construct allows visualization of the spine anatomy directly. Furthermore, a retractor configured in accordance with the present invention can be built off of the pedicle screw assemblies and attached pedicle screw extenders ensures ideal placement of the retractor for additional procedures that are often required (e.g., decompression, interbody device placement, etc).

In the preceding detailed description, reference has been made to the accompanying drawings that form a part hereof, and in which are shown by way of illustration specific embodiments in which the present invention may be practiced. These embodiments, and certain variants thereof, have been described in sufficient detail to enable those skilled in the art to practice embodiments of the present invention. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A method for performing surgery, comprising:
providing a pedicle screw apparatus having a first end portion of a pedicle screw extender engaged with a fixation rod receiving body of a pedicle screw assembly, wherein the pedicle screw extender is engaged in a manner allowing simultaneous transfer of rotational torque applied thereto to a screw portion of the pedicle screw assembly and maintaining a longitudinal axis of the fixation rod receiving body in substantially coincidental alignment with a longitudinal axis of the screw portion;
positioning a blade body within a minimally invasive access opening in tissue at a surgery site of a patient;
anchoring the pedicle screw assembly to a bony structure of the patient through the minimally invasive access opening, wherein said anchoring includes using the pedicle screw extender to apply rotational torque to the screw portion of the pedicle screw assembly
engaging the blade body with the pedicle screw extender in a manner limiting relative movement of the blade body relative to the pedicle screw extender; and
decoupling the blade body from the blade body surround in conjunction with engaging the retractor attachment structure at the second end portion of the blade body with the blade body mounting structure of the retractor.

2. The method of claim 1, further comprising:
engaging a retractor attachment structure at the second end portion of the blade body with a blade body mounting structure of a retractor after anchoring the pedicle screw assembly to the bony structure.

3. The method of claim 1 wherein engaging the blade body with the pedicle screw extender in a manner limiting relative movement of the blade body relative to the pedicle screw extender includes at least one of:
engaging a blade assembly retainer with the blade body after anchoring the pedicle screw assembly to a bony structure for limiting axial movement of the blade body along a longitudinal axis of the pedicle screw extender in a direction away from the bony structure; and
engaging an alignment member of the blade body within a mating alignment groove of the pedicle screw extender for limiting relative rotation of the blade body with respect to the pedicle screw extender.

4. The method of claim 1, further comprising:
dilating tissue surrounding the minimally invasive access opening using a dilator including the blade body and a blade body surround coupled to the blade body, wherein said dilating is performed prior to anchoring the pedicle screw assembly to a bony structure and wherein said anchoring is performed through a central passage of the dilator.

5. The method of claim 1, further comprising:
engaging a retractor attachment structure at the second end portion of the blade body with a blade body mounting structure of a refractor after anchoring the pedicle screw assembly to the bony structure.

6. The method of claim 5 wherein engaging the blade body with the pedicle screw extender in a manner limiting relative movement of the blade body relative to the pedicle screw extender includes at least one of:
engaging a blade assembly retainer with the blade body after anchoring the pedicle screw assembly to a bony structure for limiting axial movement of the blade body along a longitudinal axis of the pedicle screw extender in a direction away from the bony structure; and
engaging an alignment member of the blade body within a mating alignment groove of the pedicle screw extender for limiting relative rotation of the blade body with respect to the pedicle screw extender.

7. A method for performing minimally invasive surgery, comprising:
engaging a first end portion of a pedicle screw extender with a fixation rod receiving body of a pedicle screw assembly, wherein the pedicle screw extender is engaged in a manner allowing simultaneous transfer of rotational torque applied thereto to a screw portion of the pedicle screw assembly and maintaining a longitudinal axis of the fixation rod receiving body in substantially coincidental alignment with a longitudinal axis of the screw portion;
dilating tissue surrounding a minimally invasive access opening in tissue at a surgery site of a patient using a dilator having the blade body integral therewith, wherein the dilator has a central passage extending therethrough;
anchoring the pedicle screw assembly to a bony structure of the patient through the central passage of the dilator, wherein said anchoring includes using the pedicle screw extender to apply rotational torque to the screw portion of the pedicle screw assembly;
coupling the blade body to the pedicle screw extender for at least one of limiting axial movement of the blade body along a longitudinal axis of the pedicle screw extender in a direction away from the bony structure and limiting relative rotation between the blade body and the pedicle screw extender after anchoring the pedicle screw assembly to a bony structure; and
engaging a retractor attachment structure at the second end portion of the blade body with a blade body mounting structure of a retractor after coupling the blade body to the pedicle screw extender, wherein said engaging the retractor attachment structure of the blade body with the blade body mounting structure of the retractor includes detaching the blade body surround from the retractor attachment structure of the blade body and engaging the retractor attachment structure of the blade body with the blade body mounting structure of the retractor.

8. The method of claim 7 wherein coupling the blade body with the pedicle screw extender includes:
engaging an alignment member of the blade body within a mating alignment groove of the pedicle screw extender for limiting relative rotation between the blade body and the pedicle screw extender; and
engaging a blade assembly retainer with the blade body for limiting axial movement of the blade body along a longitudinal axis of the pedicle screw extender in a direction away from the bony structure.

9. The method of claim 8 wherein:
said dilating is performed using a dilator a blade body surround coupled to the blade body;

the blade body and the blade body surround jointly define a central passage of the dilator; and said anchoring of the pedicle screw assembly is performed through the central passage of the dilator.

10. The method of claim 7 wherein:

said dilating is performed using a dilator a blade body surround coupled to the blade body;

the blade body and the blade body surround jointly define a central passage of the dilator; and said anchoring of the pedicle screw assembly is performed through the central passage of the dilator.

11. A method for performing minimally invasive surgery, comprising:

dilating tissue surrounding a minimally invasive access opening in tissue at a surgery site of a patient by sequentially inserting each one of a series of dilators into the access opening, wherein a particular one of said dilators encompasses an immediately prior inserted one of said dilators, and wherein a last inserted one of said dilators includes a blade body surround detachably attached to a blade body to jointly define a central passage of the last inserted one of said dilators within which the immediately prior inserted one of said dilators is positioned;

removing all of said prior inserted ones of said dilators from within the central passage of the last inserted one of said dilators such that the last inserted one of said dilators remains within the access opening;

anchoring a pedicle screw assembly to a bony structure of a patient through the central passage of the last inserted one of said dilators, wherein said anchoring includes using the pedicle screw extender to apply rotational torque to the screw portion of the pedicle screw assembly;

coupling the blade body to the pedicle screw extender for at least one of limiting axial movement of the blade body along a longitudinal axis of the pedicle screw extender in a direction away from the bony structure and limiting relative rotation between the blade body and the pedicle screw extender after anchoring the pedicle screw assembly to a bony structure; and engaging a retractor attachment structure at the second end portion of the blade body with a blade body mounting structure of a refractor after anchoring the pedicle screw assembly to the bony structure.

12. The method of claim 11 wherein coupling the blade body with the pedicle screw extender includes:

engaging an alignment member of the blade body within a mating alignment groove of the pedicle screw extender for limiting relative rotation between the blade body and the pedicle screw extender; and engaging a blade assembly retainer with the blade body for limiting axial movement of the blade body along a longitudinal axis of the pedicle screw extender in a direction away from the bony structure.

13. The method of claim 12 wherein said engaging the retractor attachment structure of the blade body with the blade body mounting structure of the retractor includes:

detaching the blade body surround from the retractor attachment structure of the blade body; and engaging the retractor attachment structure of the blade body with the blade body mounting structure of the retractor.

14. The method of claim 11 wherein said engaging the retractor attachment structure of the blade body with the blade body mounting structure of the retractor includes:

detaching the blade body surround from the retractor attachment structure of the blade body; and engaging the retractor attachment structure of the blade body with the blade body mounting structure of the retractor.

15. The method of claim 11 wherein engaging the retractor attachment structure with the blade body mounting structure is performed after coupling the blade body to the pedicle screw extender.

16. The method of claim 15 wherein coupling the blade body with the pedicle screw extender includes:

engaging an alignment member of the blade body within a mating alignment groove of the pedicle screw extender for limiting relative rotation between the blade body and the pedicle screw extender; and engaging a blade assembly retainer with the blade body for limiting axial movement of the blade body along a longitudinal axis of the pedicle screw extender in a direction away from the bony structure.

* * * * *